United States Patent [19]
Papavassiliou et al.

[11] Patent Number: 5,952,523
[45] Date of Patent: Sep. 14, 1999

[54] METHOD FOR PRODUCING VINYL ACETATE

[75] Inventors: Vasilis Papavassiliou, Kent; Matthew Lincoln Wagner, White Plains, both of N.Y.; Roger William Day, Southbury, Conn.

[73] Assignee: Praxair Technology, Inc., Danbury, Conn.

[21] Appl. No.: 09/001,558

[22] Filed: Dec. 31, 1997

Related U.S. Application Data

[63] Continuation-in-part of application No. 08/899,706, Jul. 24, 1997.

[51] Int. Cl.[6] .................................................... C07C 67/00
[52] U.S. Cl. ........................................ 560/241.1; 560/242
[58] Field of Search ................................. 560/241.1, 242

[56] References Cited

U.S. PATENT DOCUMENTS

| | | | |
|---|---|---|---|
| 3,083,213 | 3/1963 | Courter | 260/348.5 |
| 3,119,837 | 1/1964 | Kingsley et al. | 260/348.5 |
| 4,066,713 | 1/1978 | Faraci et al. | 560/242 |
| 4,769,047 | 9/1988 | Dye | 55/26 |
| 4,904,807 | 2/1990 | Ozero | 549/534 |
| 5,179,056 | 1/1993 | Bartley | 560/241.1 |
| 5,179,057 | 1/1993 | Bartley | 560/241.1 |
| 5,189,004 | 2/1993 | Bartley | 560/241.1 |
| 5,262,551 | 11/1993 | Horrell, Jr. et al. | 549/534 |
| 5,466,837 | 11/1995 | Ramachandran et al. | 560/241.1 |

OTHER PUBLICATIONS

Borman et al., "An Experimental Study of the Kinetics of the Selective Oxidation of Ethene over a Silver on a–Alumina Catalyst" Ind. Eng. Chem Res, 1995, vol. 34, pp. 49–58.

*Primary Examiner*—Amelia Owens
*Attorney, Agent, or Firm*—Bernard Lau

[57] ABSTRACT

A method for producing vinyl acetate using ethylene, acetic acid and argon containing oxygen that maximizes selectivity and minimizes ethylene loses to purge.

16 Claims, 1 Drawing Sheet

METHOD FOR PRODUCING VINYL ACETATE

This is a Continuation-in-Part of prior U.S. application Ser. No. 08/899,706 filing date: Jul. 24, 1997.

FIELD OF THE INVENTION

This invention relates to a method for producing vinyl acetate, and more particularly to a method for producing vinyl acetate that maximizes selectivity and minimizes ethylene lost to purge.

BACKGROUND OF THE INVENTION

Vinyl acetate is produced commercially by the catalyzed partial oxidation of ethylene in the presence of acetic acid and oxygen. The oxygen source may be commercially available oxygen or air. Generally, in an oxygen-based process, ethylene, acetic acid and oxygen are mixed with a recycle gas and fed to the reactor. The reactor comprises a number of tubes which are placed inside a vessel and arranged similar to shell and tube heat exchangers. The reactor tubes are filled with preferably a metallic catalyst on a porous support containing small amounts of promoters. A coolant circulates in the shell around the reactor tubes to maintain temperature control.

In an oxygen-based process, a typical composition of the gas stream that is fed to the reactor tubes includes 40 to 60 mol % ethylene, 5 to 10 mol % oxygen, 4 to 10 mol % argon, 10 to 15 mol % acetic acid, 5 to 15 mol % carbon dioxide, with ethane, nitrogen and water constituting the remainder of the composition.

Ethylene and acetic acid react with oxygen to form vinyl acetate and also in a side reaction to form carbon dioxide and water. Both reactions are exothermic. The reactor effluent is treated in two separate steps by removing product vinyl acetate and remaining reactant acetic acid, and by removing byproduct carbon dioxide. The remaining gas is recycled after a portion of it is purged. The purge stream is required in order to keep impurities in the reactor at acceptable levels. Impurities, like argon, are introduced in the oxygen stream, and like ethane or propane, in the ethylene feed stream. A significant amount of ethylene is lost in the purge stream as a selectivity loss. Typically, a purge gas composition is 65.0 mol % ethylene, 7.0 mol % oxygen, 5.0 mol % argon, 17.8 mol % carbon dioxide, 4.0 mol % nitrogen, and the remaining being ethane and methane.

In general, argon impurities introduced with the oxygen stream determine the size of the purge stream when oxygen concentration of the oxygen feed is between 98 mol % and 99.6 mol %. If the amount of argon introduced in the reactor decreases, then the size of the purge stream can be lowered and ethylene loses can be reduced. An oxygen feed with higher oxygen concentration (>99.6 mol %) will result in reduction of the purge volumetric flow rate if argon is the impurity that controls the purge. However, other impurities are also introduced in the process. For example, because of the corrosive nature of the acetic acid in the process, the instruments that are used for process control require nitrogen purge/blowback. Nitrogen is the inert gas of choice and ends up in the recycle. Nitrogen must therefore be removed with the purge to prevent nitrogen from building up in the recycle. If nitrogen enters the reactor in amounts similar to those of argon, then steps must be taken to reduce the nitrogen concentration before reducing the argon concentration.

Various methods for treating the purge from oxygen-based reactions to recover ethylene have been proposed. For example, U.S. Pat. No. 4,904,807 discloses the use of an argon selective membrane that is used to treat the purge and separate it into two streams 1) an argon rich stream that is vented and 2) an ethylene rich stream that can be recycled back to the ethylene oxide reactor, and U.S. Pat. No. 4,769,047 discloses the use of pressure swing adsorption to remove ethylene from the purge and recycle it back to the reactor. A major disadvantage in these methods is the large capital cost of the associated equipment.

It is believed that there has not been a commercially practical solution to reduce the impurities associated with the production of vinyl acetate. Therefore, there is a need to provide a new method for producing vinyl acetate which maximizes the selectivity and minimizes ethylene loses to purge, thus improving the yield of the vinyl acetate production.

OBJECTS OF THE INVENTION

It is therefore an object of the invention to provide a method for improving the yield of the oxygen-based process in vinyl acetate production.

It is another object to provide a method for producing vinyl acetate which maximizes the selectivity and minimizes loses to purge.

It is yet another object to provide a method for increasing the selective production of vinyl acetate by adjusting the concentration of at least one of ethylene, acetic acid, oxygen, nitrogen and carbon dioxide.

SUMMARY OF THE INVENTION

This invention is directed to a method for enhancing the yield of vinyl acetate production comprising combining ethylene, acetic acid and argon-containing oxygen stream with a recycle gas to form a gaseous reaction mixture; feeding a stream of reaction mixture into a catalyst filled reactor such that a reaction effluent stream emerges therefrom; passing the reaction effluent stream to a scrubbing unit such that a vinyl acetate-acetic acid mixture effluent stream and an ethylene-rich effluent stream emerge therefrom; passing a portion of the ethylene-rich effluent stream to purge as a purge stream and at least a portion of the ethylene-rich effluent stream to a carbon dioxide removal unit such that carbon dioxide effluent stream and a carbon dioxide-free ethylene-rich effluent emerges therefrom; passing a portion of the stream of carbon dioxide-free ethylene-rich effluent stream with the ethylene-rich effluent stream to form the recycle gas; passing the vinyl acetate-acetic acid mixture effluent stream to a purification unit such that an acetic acid recycle stream and vinyl acetate stream emerge therefrom; and passing the acetic acid recycle stream with the acetic acid.

For purposes of this invention, the gaseous constituents preferably comprises 40–60 mol % ethylene, 5–10 mol % oxygen, 4–10 mol % argon, 10–15 mol % acetic acid, and 5–15 mol % carbon dioxide. The catalyst filled reactor comprises a reactor tube filled with palladium and gold on a porous support.

BRIEF DESCRIPTION OF THE DRAWINGS

Other objects, features and advantages will occur to those skilled in the art from the following description of preferred embodiments and the accompanying drawings, in which.

DETAILED DESCRIPTION OF THE INVENTION

Figure 1:
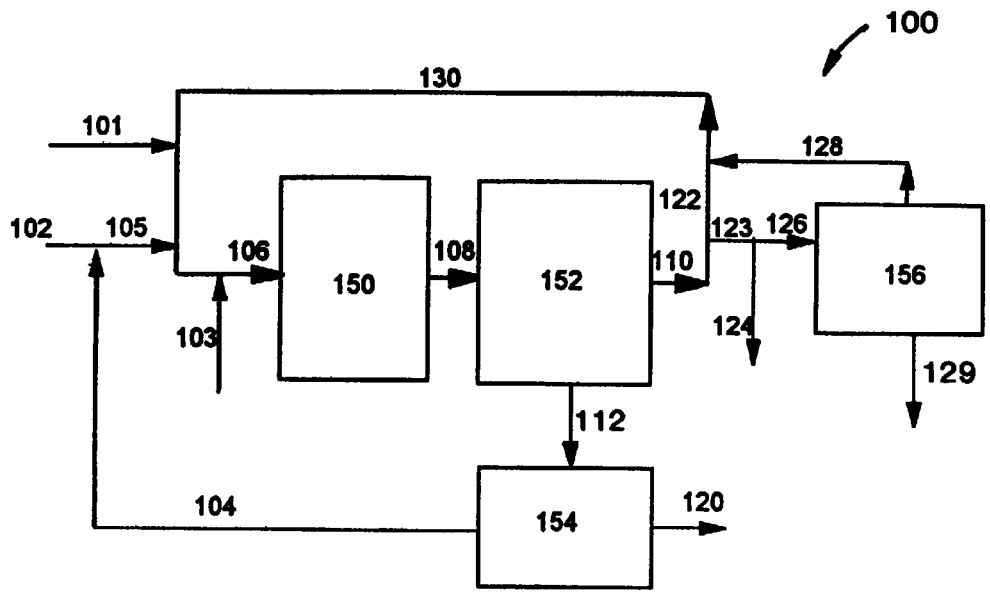
FIG. 1 is a schematic representation of a process for producing vinyl acetate by selective oxidation of ethylene and acetic acid with oxygen.

FIG. 1 provides a schematic representation 100 of a process for producing vinyl acetate by the selective oxidation of ethylene and acetic acid with oxygen. Acetic acid 102 combines with acetic acid recycle stream 104 forming acetic acid stream 105. Ethylene 101, argon-containing oxygen 103 and acetic acid stream 105 are added to ethylene recycle stream 130 forming ethylene-acetic acid-oxygen stream 106, which is fed into reactor 150. Emerging from reactor 150 is stream 108 which is passed to a scrubbing unit 152. Emerging from the scrubbing unit 152 are two streams: 1) ethylene rich stream 110, and 2) stream 112 containing vinyl acetate and acetic acid. Ethylene rich stream 110 is separated into streams 122 and 123. Stream 123 is further divided into purge stream 124, and stream 126 for passing through carbon dioxide removal unit 156. Purge stream 124 is removed. Purified carbon dioxide stream 129 and carbon dioxide-free ethylene effluent stream 128 emerge from carbon dioxide removing unit 156. Purified carbon dioxide stream 129 is removed. Carbon dioxide free ethylene rich effluent stream 128 is added to stream 122 forming recycle stream 130.

Vinyl acetate monomer and acetic acid containing stream 112 is passed into purification unit 154. Emerging from unit 154 therefrom are acetic acid recycle stream 104 and vinyl acetate stream 120. Vinyl acetate stream is removed as a product.

In an oxygen-based process, argon impurities introduced with the oxygen stream determine the size of the purge stream for oxygen purity between 98 mol % to 99.6 mol %. The amount of argon that is removed in the purge equals the product of the argon concentration in the purge times the purge volume and this product must be equal to the amount of argon that is added to the reactor by the fresh oxygen feed according to the equation (1) below:

$$\text{(volumetric argon argon concentration)} \times \text{(volumetric purge purge rate)} = \text{(volume of argon added by the fresh oxygen feed)} \quad (1)$$

If the amount of argon introduced to the process by the fresh oxygen feed decreases and argon concentration remains constant, then, according to equation (1), the size of the purge stream can be lowered and ethylene lost to the purge can be reduced. If the amount of argon introduced to the process decreases and argon concentration is reduced, then the size of the purge stream will be increased relative to the constant argon case.

Figure 2:
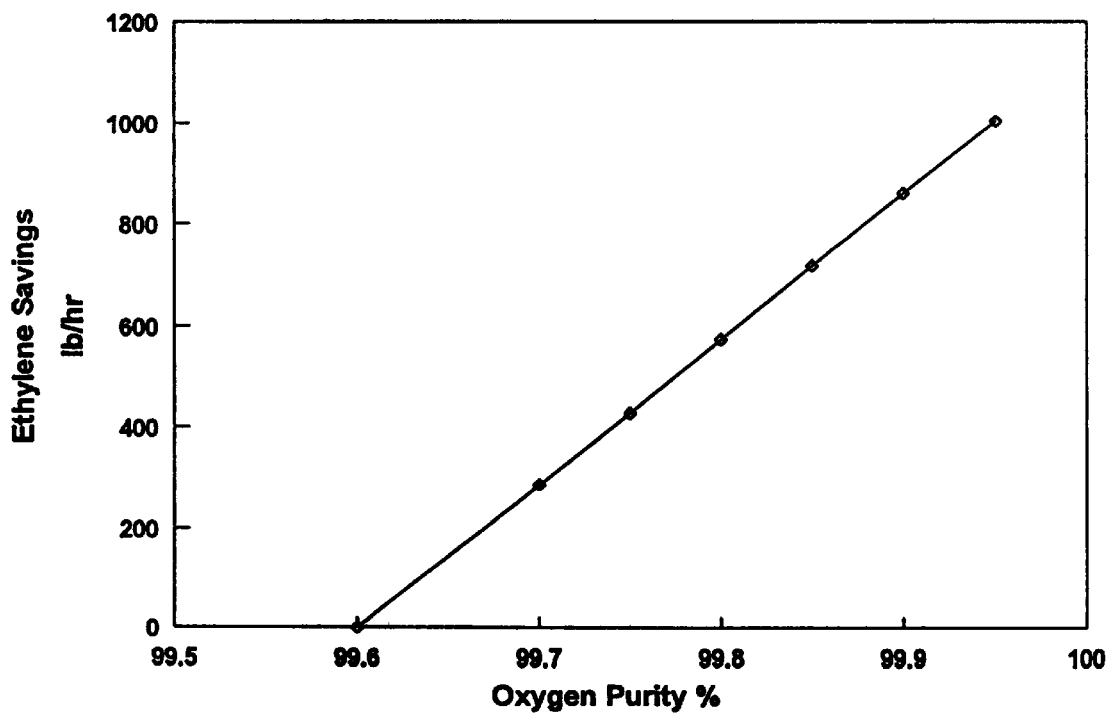
FIG. 2 is a graphical representation of the effects of the savings to ethylene and of reducing the volume of the purge stream thereby when the oxygen concentration increases from 99.6% oxygen to 99.95% oxygen, and when the argon concentration in the recycle stream is maintained at a constant 5%.

In the vinyl acetate manufacturing process, if argon is the impurity that controls the volume of the purge then if the oxygen concentration in the oxygen feed can be increased then the purge volumetric flow rate can be reduced resulting in substantial ethylene savings. For example, a plant producing 800 MM lb/yr vinyl acetate is used to demonstrate this invention. The gas stream that is fed to the reactor tubes is filled with palladium and gold on a porous support. FIG. 2 represents the reduction in the volume of the purge stream and the ethylene savings from 99.6 mol % oxygen purity to 99.95 mol % purity oxygen, and keeping the argon concentration in the recycle stream at 5 mol %. An argon containing oxygen stream that contains more than 99.6 mol % oxygen is defined for the purpose of this invention as high purity oxygen. In FIG. 2, the purge gas composition is 65.0 mol % ethylene, 7.0 mol % oxygen, 5.0 mol % argon, 20.5 mol % carbon dioxide, with the rest being ethane and methane. At 99.95 mol % oxygen purity the ethylene saved represents about 2.5 mol % of the ethylene that is fed to the process, which is a significant improvement for an industrial process.

Reducing the purge flow, while keeping the argon concentration in the recycle gas constant, reduces the ethylene losses in the purge. Instead of keeping the argon concentration constant and reducing purge flow rate, this invention also provides a method for reducing the argon concentration using high purity oxygen and adjusting the purge flow. This type of operation can be used even if other impurities are present that control the purge. Reducing the argon concentration enables the increase of ethylene, acetic acid, oxygen or carbon dioxide concentration, or a combination of these four gases to obtain a reactor feed gas composition with better heat transport properties. If the argon concentration decreases and is replaced by ethylene or carbon dioxide, then the oxygen concentration can also be increased because argon has an adverse effect on flammability. See, U.S. Pat. No. 3,855,280. Increasing the oxygen concentration improves the reactor yield. The reaction rates for the desired vinyl acetate formation depend on the concentration of all reactant and products. Adjusting the concentrations of reactants and products in the feed can result in an increased yield of vinyl acetate. The purge flow rate may still be smaller than that employed when high purity oxygen is not used, thus providing additional ethylene savings.

There are two reasons for selectivity improvement if the argon concentration decreases: 1) better heat transport properties of the gas fed to the reactor that will reduce the hot spot effect and improve selectivity, and 2) better kinetics through adjusting the remaining gases (reactants and products) concentrations. Improving the selectivity to vinyl acetate means more ethylene, acetic acid and oxygen that are fed to the reactor are converted to vinyl acetate and less to byproducts. The improvement depends on a variety of conditions including the type and age of the catalyst, and various operating conditions like temperature, pressure and residence time inside the reactor tubes, and the temperature, pressure and flow rate of the coolant fluid flowing in the shell around the reactor tubes.

The selectivity improvement must be determined on a case by case basis because of the differences in the catalyst and the operating conditions used by each commercial plant.

For the reasons outlined above, when high purity oxygen is used, vinyl acetate selectivity improvement from 0.05 mol % to 1 mol % can be expected for every 1 mol % reduction of the argon concentration if at the same time a combination of the other gas concentrations are increased to replace that of argon. However, reducing the argon concentration will increase the purge flow rate and may also increase the ethylene concentration in the recycle stream, and consequently increase ethylene losses in the purge. Thus, when high purity oxygen is used, there exists an optimum reduced argon concentration in the recycle stream and purge stream flow-rate that will maximize ethylene yield.

If other impurities are introduced in the process in significant amounts, then additional steps must be taken to remove the impurities before lowering the purge stream flow rate. For example, the nitrogen that is used for instrumentation protection can be replaced with carbon dioxide (another inert gas). The carbon dioxide that replaces nitrogen increases the carbon dioxide concentration in the recycle stream. Additional carbon dioxide in the recycle stream raises the carbon dioxide concentration, which will improve the performance of the carbon dioxide removal section (see FIG. 1). The carbon dioxide removal unit may not remove all of the additional carbon dioxide and, as a result, the carbon dioxide concentration in the recycle stream that is fed to the reactor may increase. Thus, carbon dioxide will replace nitrogen in the stream that is fed to the reactor. Carbon dioxide has better heat transport properties than nitrogen, thus, a lower concentration of nitrogen and a higher concentration of carbon dioxide are beneficial for the reactor's performance. The carbon dioxide can be supplied from the product of the carbon dioxide removal section or from an independent source. The nitrogen removal reduces the purge requirements. Reducing the nitrogen concentration means that we can increase ethylene, acetic acid or oxygen concentration or a combination of the four to obtain a reactor feed gas composition with better heat transport properties and better reaction kinetics. The void left by the decrease in nitrogen concentration can be replaced by ethylene, carbon dioxide and oxygen. Increasing the ethylene, carbon dioxide and oxygen concentrations improves the reactor yield.

This invention provides a number of clear advantages over the art by reducing the amount of argon in the system and/or that is introduced in the system. One embodiment uses high purity oxygen and adjusts the volume of the purge stream to effectively reduce the argon concentration. Another embodiment uses carbon dioxide to replace nitrogen in the system, and reduce the nitrogen concentration. In another embodiment, one can replace nitrogen with carbon dioxide, use high purity oxygen and reduce the volume of the purge stream.

Improving the selectivity of the reactor by reducing the concentration of at least one of argon or nitrogen could potentially allow the increase of vinyl acetate production. If the ethylene feed rate was held constant and the selectivity improved, additional vinyl acetate would necessarily be produced. That is, an embodiment of this invention consists of keeping the flow rate constant, while adjusting the concentration of at least one of ethylene, acetic acid and argon-containing oxygen. If the downstream separation equipment could process the additional load, this would be a zero capital method of increased production. Production increases in the order of about 0.5–5% total yield can be expected.

Reducing the concentration of at least one of argon or nitrogen also reduces the effects of hot spot formation in the reactor and thus extend the catalyst life. This effect is associated with improving selectivity (which reduces the amount of heat generated within the reactor) and improving the thermal properties of the reaction gas mixture (which improves the heat removal from the reactor). Extension of a catalyst life will reduce the consumption of the catalyst. It is expected that the catalyst life may be extended up to about a year. In the reaction, the gas stream is fed to the reactor tubes filled with palladium and gold on a porous support.

The catalysts employed in the process of this invention may be a metal-containing catalysts known in the art for catalyzing the controlled oxidation of ethylene with acetic acid and molecular oxygen to produce vinyl acetate. The catalysts may be a metal, preferably palladium and gold on a suitable support, preferably porous support. The support may be comprised of a siliceous and aluminous materials. Particularly suitable catalysts are those made of essentially gold metal and promoters on low surface area supports containing alpha alumina along with minor proportions of silica, silicon carbide, and other refractory materials.

In general, the operating temperature of this invention suitably takes place in the range of from about 150° C. to about 350° C., preferably in the range of from about 120° C. to about 200° C.

The operating pressure for the practice of this invention is suitably in the range of from about 40 psig to about 300 psig, and preferably from about 80 to 200 psig. The space velocity is chosen according to the desired amount of production, and preferably in the range of from about 3000 to about 5000 $hr^{-1}$. These range of parameters are typically used in the current commercial vinyl acetate production.

The use of high purity oxygen in this invention may also be practiced with a conventional ethylene recovery apparatus for the purge stream, such as membrane separation or pressure swing adsorption, or cold box, to treat the purge, recover the remaining ethylene and return it to the reactor. The use of high purity oxygen greatly reduces the required capital investment for such systems.

Specific features of the invention are shown in the drawing for convenience only, as each feature may be combined with other features in accordance with the invention. Alternative embodiments will be recognized by those skilled in the art and are intended to be included within the scope of the claims.

What is claimed is:

1. A method for enhancing the yield of vinyl acetate by reducing the concentration of argon during vinyl acetate production, said method comprising
   a) combining ethylene, acetic acid and argon-containing oxygen stream with a recycle gas to form a gaseous reaction mixture;
   b) feeding a stream of said reaction mixture into a catalyst filled reactor such that a reaction effluent stream emerges therefrom;
   c) passing said reaction effluent stream to a scrubbing unit such that a vinyl acetate-acetic acid mixture effluent stream and an ethylene-rich effluent stream emerge therefrom;
   d) passing a portion of said ethylene-rich effluent stream to purge as a purge stream and a portion of said ethylene-rich effluent stream to a carbon dioxide removal unit such that carbon dioxide effluent stream and a carbon dioxide-free ethylene-rich effluent stream emerge therefrom;
   e) passing a portion of said stream of carbon dioxide-free ethylene-rich effluent stream with said ethylene-rich effluent stream to form said recycle gas;
   f) passing said vinyl acetate-acetic acid mixture effluent stream to a purification unit such that an acetic acid recycle stream and a vinyl acetate stream emerge therefrom;
   g) combining said acetic acid recycle stream with said acetic acid stream;
   h) increasing the oxygen content of said argon-containing oxygen stream; and
   i) adjusting the flow of the purge stream to effectively reduce the concentration of argon.

2. The method of claim 1 wherein step (i) further comprises adjusting the feed flow rate of at least one of said ethylene, acetic acid and argon-containing oxygen streams to increase the selective production of said vinyl acetate.

3. The method of claim 1 wherein step (i) comprises keeping the flow rate constant and adjusting the concentration of at least one of the ethylene, acetic acid and argon-containing oxygen.

4. The method of claim 1 wherein step (i) further comprises producing a gas with enhanced heat transport properties to reduce the effects of hot spots formed in the reactor.

5. The method of claim 4 wherein the reduction in the effects of said hot spots increases the selectivity to vinyl acetate and increases catalyst life.

6. The method of claim 1 wherein said catalyst filled reactor comprises reactor tubes filled with palladium and gold on a porous support.

7. A method for producing vinyl acetate comprising
  a) combining ethylene, acetic acid and argon-containing oxygen streams with a recycle gas to form a gaseous reaction mixture;
  b) feeding a stream of said reaction mixture into a catalyst filled reactor such that a reaction effluent stream emerges therefrom;
  c) passing said reaction effluent stream to a scrubbing unit such that a vinyl acetate-acetic acid mixture effluent stream and an ethylene-rich effluent stream emerge therefrom;
  d) passing a portion of said ethylene-rich effluent stream to purge as a purge stream and a portion of said ethylene-rich effluent stream to a carbon dioxide removal unit such that carbon dioxide effluent stream and a carbon dioxide-free ethylene-rich effluent stream emerge therefrom;
  e) passing a portion of said carbon dioxide-free ethylene-rich effluent stream with said ethylene-rich effluent stream to form said recycle gas;
  f) passing said vinyl acetate-acetic acid mixture effluent stream to a purification unit such that an acetic acid recycle stream and vinyl acetate stream emerge therefrom;
  h) combining said acetic acid recycle stream with said acetic acid stream;
  i) passing a portion of carbon dioxide to replace nitrogen for instrument purge/blowback; and
  j) increasing the oxygen content of said argon-containing oxygen stream.

8. The method of claim 7 comprising reducing the flow rate of the purge stream.

9. The method of claim 7 wherein the feed gas introduced in the reaction zone comprising 40–80 mol % ethylene, 5–15 mol % oxygen, 0–10 mol % argon, 10–15 mol % acetic acid, and 5–15 mol % carbon dioxide.

10. The method of claim 7 wherein said catalyst filled reactor comprises reactor tubes filled with palladium and gold on a porous support.

11. A method for producing vinyl acetate comprising
  a) combining ethylene, acetic acid and argon-containing oxygen streams with a recycle gas to form a gaseous reaction mixture;
  b) feeding a stream of said reaction mixture into a catalyst filled reactor such that a reaction effluent stream emerges therefrom;
  c) passing said reaction effluent stream to a scrubbing unit such that a vinyl acetate-acetic acid mixture effluent stream and an ethylene-rich effluent stream emerge therefrom;
  d) passing a portion of said ethylene-rich effluent stream to purge as a purge stream and a portion of said ethylene-rich effluent stream to a carbon dioxide removal unit such that a carbon dioxide effluent stream and a carbon dioxide-free ethylene-rich effluent stream emerge therefrom;
  e) passing a portion of said stream of carbon dioxide-free ethylene-rich effluent stream with said ethylene-rich effluent stream to form said recycle gas;
  f) passing said vinyl acetate-acetic acid mixture effluent stream to a purification unit such that an acetic acid recycle stream and vinyl acetate stream emerge therefrom;
  h) passing said acetic acid recycle stream with said acetic acid stream; and
  i) passing a stream of carbon dioxide to replace nitrogen for instrument purge/blowback to effectively reduce the nitrogen concentration in the system.

12. The method of claim 11 wherein step (i) further comprises adjusting the feed flow rate of at least one of said ethylene, acetic acid and argon-containing oxygen stream, thereby increasing the selective production of said vinyl acetate.

13. The method of claim 11 wherein step (i) further comprises producing a gas with enhanced heat transport properties to reduce the effects of hot spots formed in the reactor.

14. The method of claim 11 wherein the reduction in the effects of said hot spots increases the selectivity to vinyl acetate and increases catalyst life.

15. The method of claim 11 wherein the feed gas introduced in the reaction zone comprising 40–80 mol % ethylene, 5–15 mol % oxygen, 0–10 mol % argon, 10–15 mol % acetic acid, and 5–15 mol % carbon dioxide.

16. The method of claim 11 wherein said catalyst filled reactor comprises reactor tubes filled with palladium and gold on a porous support.

* * * * *

(12) REEXAMINATION CERTIFICATE (4698th)
United States Patent
Papavassiliou et al.

(10) Number: US 5,952,523 C1
(45) Certificate Issued: Dec. 31, 2002

(54) METHOD FOR PRODUCING VINYL ACETATE

(75) Inventors: Vasilis Papavassiliou, Kent, NY (US); Matthew Lincoln Wagner, White Plains, NY (US); Roger William Day, Southbury, CT (US)

(73) Assignee: Praxair Technology, Inc., Danbury, CT (US)

Reexamination Request:
No. 90/005,927, Feb. 14, 2001

Reexamination Certificate for:
Patent No.: 5,952,523
Issued: Sep. 14, 1999
Appl. No.: 09/001,558
Filed: Dec. 31, 1997

Related U.S. Application Data

(63) Continuation-in-part of application No. 08/899,706, filed on Jul. 24, 1997.

(51) Int. Cl.[7] ............... C07C 67/00; C07C 27/10; C07C 67/04
(52) U.S. Cl. ............................... 560/241.1; 560/242
(58) Field of Search ..................... 560/241.1, 242

(56) References Cited

U.S. PATENT DOCUMENTS

| | | | |
|---|---|---|---|
| 4,879,396 A | * | 11/1989 | Ozero |
| 5,233,060 A | | 8/1993 | Pendergast et al. |
| 5,519,152 A | | 5/1996 | Gorcester |

FOREIGN PATENT DOCUMENTS

| | | |
|---|---|---|
| EP | 0-200518 A2 * | 11/1986 |
| GB | 1088730 | 10/1967 |
| GB | 1382099 | 1/1975 |

* cited by examiner

*Primary Examiner*—D. Margaret Seaman

(57) ABSTRACT

A method for producing vinyl acetate using ethylene, acetic acid and argon containing oxygen that maximizes selectivity and minimizes ethylene loses to purge.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–16 is confirmed.

* * * * *